(12) United States Patent
Bell

(10) Patent No.: US 7,001,513 B2
(45) Date of Patent: Feb. 21, 2006

(54) AUTOMATED PROCESSING OF A BIOLOGICAL COMPONENT

(75) Inventor: Craig J. Bell, E. Swanzey, NH (US)

(73) Assignee: NuVue Technologies, Inc., Keene, NH (US)

( * ) Notice: Subject to any disclaimer, the term of this patent is extended or adjusted under 35 U.S.C. 154(b) by 197 days.

(21) Appl. No.: 10/635,181

(22) Filed: Aug. 6, 2003

(65) Prior Publication Data

US 2005/0029181 A1  Feb. 10, 2005

(51) Int. Cl.
B01D 15/08 (2006.01)
(52) U.S. Cl. .............. 210/198.2; 210/656; 210/143; 604/6.01; 604/6.04; 604/6.11
(58) Field of Classification Search .............. 604/6.01, 604/6.04, 6.11; 210/102, 143, 198.2, 656, 210/659
See application file for complete search history.

(56) References Cited

U.S. PATENT DOCUMENTS

| | | | | |
|---|---|---|---|---|
| 3,996,017 A | * | 12/1976 | Kaiser | 422/70 |
| 4,911,807 A | * | 3/1990 | Burd | 204/453 |
| 5,193,990 A | | 3/1993 | Kamen et al. | 417/474 |
| 5,260,028 A | * | 11/1993 | Astle | 422/81 |
| 5,372,695 A | * | 12/1994 | Demorest | 204/603 |
| 5,989,423 A | | 11/1999 | Kamen et al. | 210/258 |
| 6,325,775 B1 | * | 12/2001 | Thom et al. | 604/6.02 |
| 6,582,386 B1 | | 6/2003 | Min et al. | 604/6.01 |
| 6,605,223 B1 | * | 8/2003 | Jorgensen et al. | 210/745 |
| 6,712,963 B1 | * | 3/2004 | Schick | 210/198.2 |

OTHER PUBLICATIONS

Castellino et al. "Human Plasminogen" Methods in Enzymology, vol. 80, pp 365-378 (1981).
Robbins et al. "Human Plasmin" Methods in Enzymology, vol. 80, pp. 379-387 (1981).
Jackson et al. "Streptokinase and Staphylokinase" Methods in Enzymology, vol. 80, pp. 387-394.
Wiman. "Human alpha2-Antiplasmin" Methods in Enzymology, vol. 80, p. 395.

* cited by examiner

*Primary Examiner*—Ernest G. Therkorn
(74) *Attorney, Agent, or Firm*—Gifford, Krass, Groh, Sprinkle, Anderson & Citkowski, P.C.

(57) ABSTRACT

A biological fluid processing device includes a multiple biological fraction container enclosing a liquid biological fraction. A rigid cassette contains at least one biological fluid processing chamber. A biological fluid processing chamber includes an affinity media chamber, a gel media chamber, a concentration chamber and a collection chamber. Tubing in fluid communication with the container and the biological fluid processing chamber is selectively compressed to provide a valving function. A programmable instrument receives the cassette and regulates the valving to control the flow of the biological fluid fraction through the device.

13 Claims, 2 Drawing Sheets

AUTOMATED PROCESSING OF A BIOLOGICAL COMPONENT

FIELD OF THE INVENTION

The present invention relates to an automated process for purification and concentration of a biological component and, in particular, the purification and concentration of plasminogen, which then can be converted to plasmin for use in surgical or therapeutic procedures.

BACKGROUND OF THE INVENTION

With concerns about identifying ever-changing strains of HIV, hepatitis, and other blood born pathogens, the use of blood bank whole blood as a source for blood components in non-emergency surgical procedures is disfavored. As a result, it is advantageous to draw blood from a patient, extract the needed blood component, and then reintroduce the blood component into the patient during a surgical procedure. Plasminogen is exemplary of a blood component that is separated from a patient's own blood and reintroduced into the patient.

Plasminogen is a component of the fibrolytic system and is the plasma-protein precursor of plasmin, a serine protease. Plasmin is well known to function in fibrinolysis and fibrinogenolysis, as well as digesting factor $IX_a$, and the activation of zymogens, among its many functions. The injection of plasmin into a human eye has been shown to induce posterior vitreous detachment, as detailed in U.S. Pat. No. 5,304,118.

While methods of isolating plasminogen are well known to the art, these methods require considerable time, skill, and expensive equipment that precluded plasmin extraction and isolation as a routine adjunct to a surgical procedure or therapy. As a result, the benefits that plasmin offers as an adjunct to surgical and/or therapeutic procedures is limited to a few medical institutions. Exemplary of these time-consuming plasminogen purification procedures are U.S. Pat. Nos. 3,943,245; 5,371,007 and Castellino, *Methods of Enzy.*, Vol. 80, 265–337 (1981).

A rapid manual method for purification of plasminogen, as disclosed in the art, utilized an affinity cartridge under syringe pressure to selectively bind a desired blood component. The affinity cartridge was then washed with an equilibration buffer followed by injecting an elution buffer therethrough containing a release agent for the desired blood component. This method is detailed in U.S. Pat. No. 6,207,066 and is capable of delivering active plasmin from a blood sample within tens of minutes. However, this method has met with limited acceptance owing to the manual steps required and the variability introduced. Thus, there exists a need for an automated process for purifying a biological component.

SUMMARY OF THE INVENTION

The present invention overcomes the previously known disadvantages of the previously known biological component separation methods by providing an automated separation, purification, and concentration of a biological component, specifically for separating a blood component for autologous usage. The automated system includes a programmable controlled instrument that interacts with a sterile disposable cassette and tubing set.

The disposable cassette consists of chambers, fluid paths, and valves. The cassette houses at least one chamber, which contains the desired blood component affinity material. The affinity material of the type, which binds with the desired biological component, is prepared prior to the time of use. L-lysine (or other protein binding component) is covalently attached to silica which has been epoxy activated. Silica is a material that can withstand very high pressure and still maintain its shape. This matrix yields low backpressure and high flow rates. One to five cubic centimeters (cc) of the lysine-silica are loaded into a cassette chamber.

An optimal second chamber housed in the cassette contains a molecular exclusion filtration media. The filtration media is of the type which allows large molecules like the desired biological component to pass through the chamber unimpeded, yet retards the passage of smaller molecular weight molecules like those used for competitive elution of the blood component from the affinity chamber. This results in a molecular separation.

An optional concentration media chamber in the cassette concentrates the desired biological component solution. The concentration media of the type which is made of crosslinked dextran with liquid absorbing and molecular exclusion properties.

Additional chambers are optionally included in the cassette to provide solution storage and transfer during the process. Other chambers can provide for the conversion of the desired biological component to its active state and provide a space for the resultant preparation to be assayed for final activity determination.

The cassette incorporates fluid paths connecting inlet and outlet fluids to the various chambers. The cassette provides the means to valve the flow of fluids to and around the cassette chambers, in addition to controlling fluids to waste and collection.

The cassette has at least one inlet and one outlet port that has tubing connected to the port. The other end of the tubing is connected to a fluid bag or bags. The inlet tubing allows the fluids, like equilibration buffer, plasma or plasma solution, and/or competitive elution solution, to be brought into the cassette and selectively to the cassette chambers. The outlet tubing allows fluids to be selectively expelled from the cassette and to a fluid waste collection bag.

The instrument contains a programmable controller of the type which is of electronic, pneumatic, or mechanical (cam) driven or a combination thereof. The controller receives inputs, such as from pushing the start button, and delivers outputs, such as turning a pump on and off, closing and opening valves, and signaling procedure completion.

With regard to isolation from plasma, blood is first drawn from the patient and the blood plasma is separated from the cellular blood elements using conventional methods, such as centrifugation. After centrifugation, the blood plasma containing the blood component is retained and the cellular blood elements are discarded. The blood plasma is collected into a syringe and transferred to the plasma fluid bag attached to the cassette. A second fluid bag attached to the cassette is loaded with equilibration buffer and a third fluid bag is loaded with an elution buffer.

The cassette is loaded into the programmable controlled instrument and the fluid bags are hung on their appropriate hooks. The power to the instrument is turned on and the start button is pushed to initialize the controller. The controller now orchestrates the pump, valves, and solenoids to route the correct fluid through the various chambers at the appropriate time and in the appropriate volumes, in order to yield the desired component in a desired concentration in a collection vial at the conclusion of the process.

A known amount of an activator is then added to the eluted blood component to obtain the desired subcomponent, such as plasmin. The blood component or subcomponent is then used as desired in the surgical or therapeutic procedure.

BRIEF DESCRIPTION OF THE DRAWING

A better understanding of the present invention will be had upon reference to the following detailed description, when read in conjunction with the accompanying drawing, wherein like reference characters refer to like parts throughout the several views, and in which.

DETAILED DESCRIPTION OF A PREFERRED EMBODIMENT OF THE PRESENT INVENTION

The present invention has utility in the processing of a biological fluid to purify a component therefrom. The present invention will be described with respect to automatically separating the blood component plasminogen from blood plasma. The plasminogen is subsequently converted into plasmin and used for surgical and/or therapeutic procedures, such as a vitrectomy and/or vitreous liquefaction. It is appreciated that other blood components are readily separated from blood utilizing the method of the present invention. These other blood components illustratively include fibrin, apolipoprotein, and antibodies.

While the present invention is detailed herein generally with respect to isolating a component from blood plasma and in particular to purification of plasminogen, it is appreciated that the present invention is also well suited for a variety of other biological component separations. These component separations illustratively include urokinase from urine, nerve growth factor from cerebrospinal fluid, and various components from cell growth media or whole blood.

Figure 1:
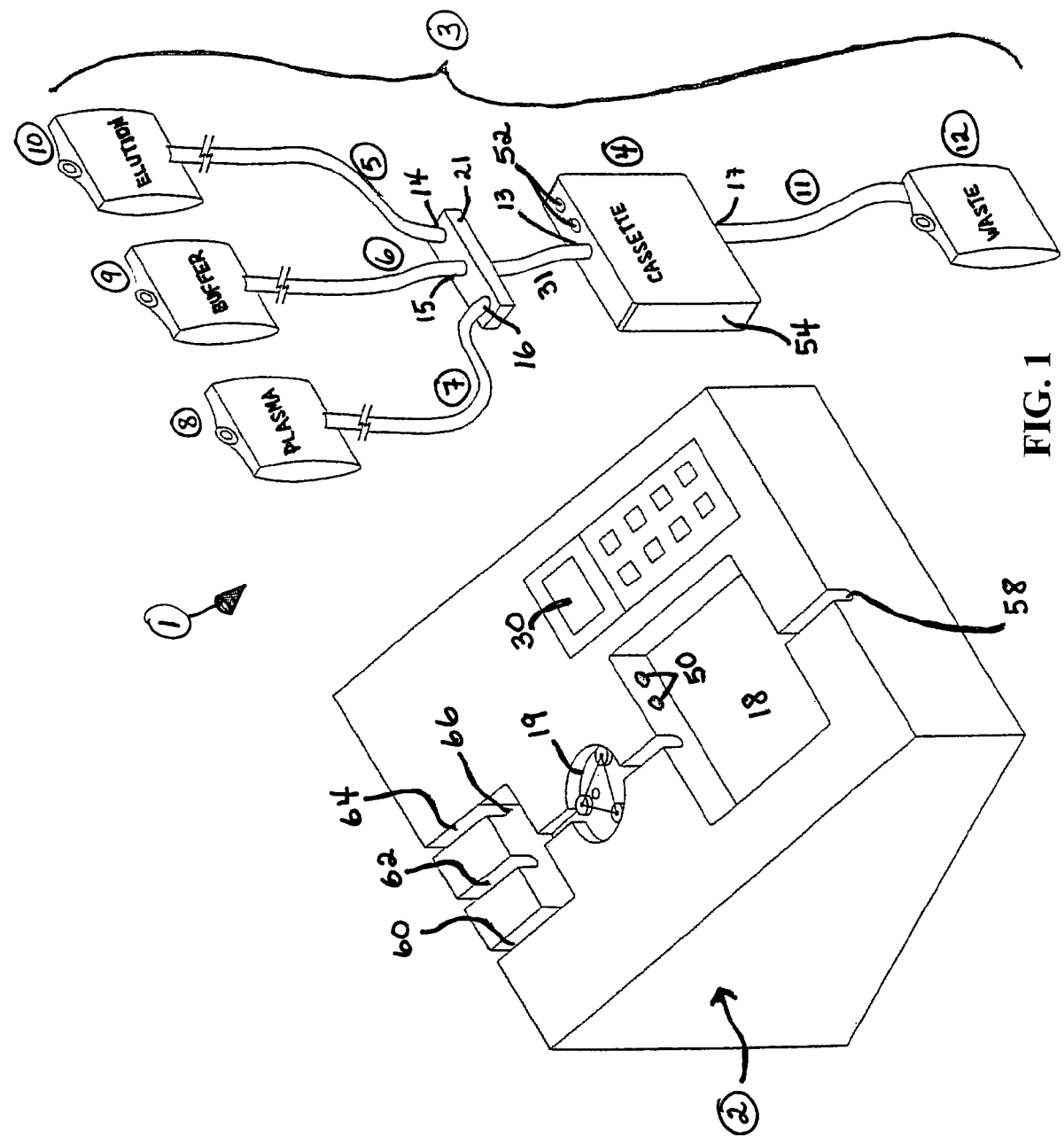
FIG. 1 is an isometric view of the system including the programmable controlled instrument and disposable cassette assembly with attached fluid lines.

With reference then to FIG. 1, the automated system to purify and concentrate plasminogen from plasma is shown as 1. System 1 is comprised of two distinct components, a programmable instrument 2, and a sterile single-use disposable cassette assembly 3. The programmable instrument 2 contains a programmable controller having a user interface 20, solenoid and/or pneumatic valve actuators 50, and a pump 19. A control panel 20 provides a user interface for programmable controller functions such as to power the instrument, start the preparation process, and monitor the parameters of the process.

The disposable cassette assembly 3 is typically made of plastic such as polypropylene, polycarbonate, or polyvinyl chloride, and includes a cassette 4 that houses at least one internal chamber and has at least one inlet port 13 and one outlet port 17. The inlet port 13 is connected to a manifold 21 through inlet pump chamber tubing 31. The manifold 21 is in fluid communication with solution containers of plasma 8, buffer 9, and elution solution 10. Preferably, the solution containers are sterile bags conventional to the blood storage art. The outlet port 17 is in fluid communication with a waste collection bag 12 via outlet tubing 11. The cassette 4 is placed into a receiving pocket 18 of programmable instrument 2, where it is selectively held therein.

Figure 2:
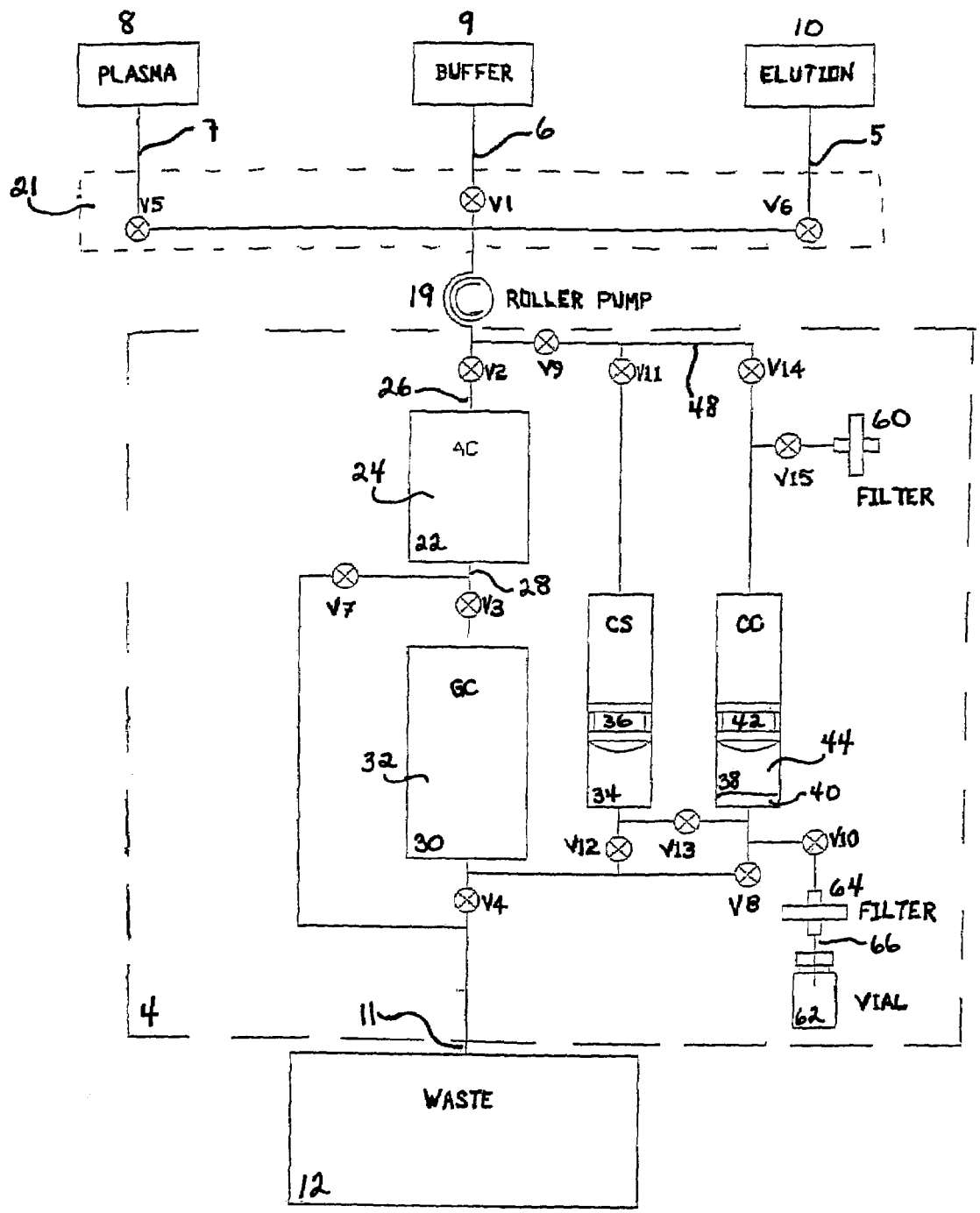
FIG. 2 is a schematic diagram illustrating the components of the preferred embodiment of the present invention.

FIG. 2 shows the preferred system components in schematic form. Cassette 4 is represented by the dotted line box shown in FIG. 2 including a rigid housing 54. The cassette 4 includes affinity media chamber 22, the chamber 22 enclosing affinity media 24. An amino acid, such as L-lysine, is affixed to the solid support offered by the affinity media 24. Affinity media chamber 22 has an inlet 26 and an outlet 28 such that all liquid injected into the inlet 26 passes through the affinity media 24 and exits through the outlet 28. The amino acid L-lysine has a high affinity to selectively adsorb the blood component plasminogen from blood plasma. The lysine (L-lysine monohydrochloride, Sigma Chemical (L-6027)) is bound to the affinity media by conventional methods and then packed into the chamber 22. Preferably, the affinity media chamber 22 is made of polypropylene with polyethylene frits. It is appreciated other species are readily bound to the affinity media 24 to selectively adsorb blood components. These species illustratively include antibodies specific to a particular blood component; platelet derived growth factor or other hormones. For example, heparin is a mucopolysaccharide sulfuric acid ester that is found in liver tissue. Heparin is active as a ligand to selectively bind fibroblast growth factor, vascular endothelial growth factor (VEGF), and platelet derived growth factor (PDGF) from cell culture media. Heparin also is active to selectively bind proteins from whole blood or plasma that are involved in the coagulation cascade such as thrombin.

The chamber 22 typically contains 1 to 5 cc packed volume of affinity media such as L-lysine bound to a rigid support such as epoxy-activated silica beads. Preferably, 2 to 4 cc of affinity medium is utilized herein. Other alternative beads can include a ceramic matrix illustratively including alumina or titania with lysine attached via an epoxy-activated linkage. The affinity media is required to withstand the application of pressure necessary for performing an inventive elution throughput without collapsing. The pressure operative herein is defined to be at least the pressure exerted by a roller pump, syringe pump, or other pump mechanisms against the back pressure induced by the affinity media. Pressures generated herein are typically 1 to 10 atmospheres. The epoxy-activated silica beads operative herein are manufactured by Waters Corporation. Such beads typically have a diameter of 40 $\mu$m, a pore size of 50 nm and a binding capacity of 3–7 $\mu$moles of lysine per (ml) of packing material.

Cassette 4 also has a gel media chamber 30 that contains gel filtration media 32, composed of cross-linked dextran beads. The gel filtration media 32 performs molecular size exclusion. The large blood component plasminogen passes through the gel media 32 comparatively unimpeded while the smaller elution molecules such as epsilon aminocaproic acid enter the pores of the gel media beads and are slowed in traversing the gel media to create a separation. In a preferred embodiment, the gel filtration medium is G-25 fine Sephadex (Amersham Biosciences). It is appreciated that other gel media are operative to filter a desired blood plasma component based upon factors including blood component molecular weight. The gel media chamber 30 typically contains 1.0 to 2.5 gms of dry gel beads 32 that swell when hydrated to fill a chamber volume of between 3.5 to 8.8 ml. Preferably, the gel media chamber 30 is made of polypropylene with polyethylene frits.

Alternatively, an ion exchange chromatography media chamber (Sigma Aldrich, Amersham, Waters) is used to molecularly filter the desired blood plasma component based on molecular charge and ionic strength. Employing this technology, the aminocaproic acid molecule forms an ionic bond to the media, displacing a hydrogen ion. The plasminogen then freely passes through the media. The collected fraction may have to be adjusted for pH as a result of the ionic exchange.

The cassette 4 also includes collection chamber 34 having movable plunger 36. Collection chamber 34 allows the collection of the plasminogen rich fraction from the elution curve exiting the gel media chamber 30. The collected fraction volume typically ranges from 1.0 ml to 5.0 ml for the processing of 0.5 to 2.0 milligrams of plasminogen.

The cassette 4 also includes a concentration chamber 38 that includes a filter net 40 (shown in FIG. 2), movable plunger 42, and concentration media 44. The concentration media 44 preferably are cross-linked dextran beads. The preferred concentration media is commercially available as dry Sephadex G-50 (Amersham Biosciences), D-salt polyacrylamide gel with a 6,000 Dalton exclusion limit (Pierce Biotechnology), or similar material. The dry quantity of concentration media 44 absorbs a known quantity of solvent thereby concentrating the plasminogen in the remaining solvent. Preferably, the quantity of concentrating media is selected to impart a plasminogen concentration of at least two. More preferably, plasminogen is concentrated by a factor of between 3 and 10. For example, 2.6 cc of eluted buffer and plasminogen yields 0.45 ml upon contacting 0.34 grams of dry G-50 Sephadex thereby increasing plasminogen concentration to a final concentration of 0.9–3.0 milligrams per milliliter. The concentrating of a blood component according to the present invention appears to rely on the ability of an immobilized substance such as a Sephadex filtration medium to absorb a well-defined quantity of a solution without absorbing or binding the plasminogen at a higher rate than volume concentration.

Flexible tubing 48 is used within the cassette 4 to provide fluid communication between the inventive chambers. Optionally, flexible tubing 48 functions as a valve when force is applied. In this way filters, collection vial(s), or test chambers optionally are isolated. Solenoid and/or pneumatic valve actuators are positioned in instrument 2 such that piston rods 50 align with openings 52 in cassette 4 overlying predetermined sections of tubing 48. The openings 52 allow the piston rods 50 to linearly travel and compress the flexible tubing 48 against the rigid housing 54 of cassette 4. Valving action is preferably signaled by the programmable controller.

The inventive process starts with a predetermined amount of blood, for example 48 cc, being removed from the patient in any conventional fashion such as by syringe or vacuum collection tubes containing an anticoagulant. The amount of blood removed from the patient varies, depending upon the final amount of the desired blood component required.

The blood plasma is separated from the cellular blood elements in any conventional fashion, such as by centrifuging. In the preferred embodiment of the invention, the blood is centrifuged at 1000 g for ten minutes at 25° C. The plasma is then collected in a sterile syringe. Typically, 10 to 30 cc of plasma is collected. For a vitrectomy, preferably 20 to 25 cc of plasma is collected.

The plasma is then transferred into a container, preferably a fluid bag 8 of disposable cassette assembly 3. Fluid bag container 9 is filled with a sterile equilibrium buffer plasma, such isotonic potassium phosphates buffer, balanced salt solution, or a dilute balanced salt solution, in a volume of between 50 ml and 250 ml. Fluid bag 10 is filled with a competitive elution solution, such as epsilon aminocaproic acid and potassium phosphate buffer, in volume of between 5 ml and 20 ml and a concentration of between 0.5 mg/ml and 10.0 mg/ml. Optionally, the plasma and/or elution solution remain in syringes that are connected to the tubing in lieu of a fluid bag.

Disposable cassette assembly 3 is loaded into the programmable instrument 2. Solution bags 8, 9, and 10 are hung so as to gravity feed the instrument 2. Tubing lines 5, 6, and 7 are placed into corresponding slots 60, 62, 64, respectively. Manifold 21 is placed in recess 66. Pump chamber 31 is fed into roller pump 19 and cassette 4 is locked in place into instrument pocket 18. Outlet tube 11 is placed in slot 58 and fluid bag 12 is positioned to collect the fluid waste transmitted by outlet tube 11.

In operation, the inventive sequence of events begins with instrument 2 being energized through the user interface control panel 20. Table 1 provides a step-by-step breakdown of the preparation process indicating fluid movements and valving of the present invention with respect to FIGS. 1 and 2. Table 1 presumes prior blood draw and fluid bag filling.

TABLE 1

Pinch valve sequence for blood component isolation

| | STEP | FLUID | \multicolumn{15}{c}{PINCH VALVE OPERATION (O = Open, X = Closed)} |
|---|---|---|---|---|---|---|---|---|---|---|---|---|---|---|---|---|---|
| | | | 1 | 2 | 3 | 4 | 5 | 6 | 7 | 8 | 9 | 10 | 11 | 12 | 13 | 14 | 15 |
| 1. | AC flush, GC hydrate & flush, to Waste | buffer | O | O | O | O | X | X | X | X | X | X | X | X | X | X | X |
| 2. | AC plasma, to Waste | plasma | X | O | X | X | O | X | O | X | X | X | X | X | X | X | X |
| 3. | AC plasma flush, to Waste | buffer | O | O | X | X | X | X | O | X | X | X | X | X | X | X | X |
| 4. | Elute & stage protein, to Waste | elution | X | O | O | O | X | O | X | X | X | X | X | X | X | X | X |
| 5. | Collected fraction to collection syringe | elution | X | O | O | X | X | O | X | X | X | X | O | O | X | O | O |
| 6. | Collection fraction to concentrator | buffer | O | X | X | X | X | X | X | X | O | X | O | X | O | X | O |
| 7. | Concentrator to vial | buffer | O | X | X | X | X | X | X | X | O | O | X | X | X | O | X |

Step 1 involves the delivery of equilibrium buffer for pre-washing of the affinity media, hydrating and washing the gel media, and delivering the passed fluids to waste. The buffer is drawn from fluid bag 9 through tubing 6 and through open valve V1. The buffer flows into manifold 21 and through pump chamber 31 driven by pump 19, through open valve V2 and into affinity media chamber 22. The buffer continues through the affinity media chamber 22 pre-washing and wetting the affinity media 24, then exiting chamber 22 flowing through open valve V3 and into gel filtration media chamber 30. The buffer is absorbed by the dry gel media 32, swelling the beads and expanding to fill chamber 30 and washing of the gel media 32 after swelling. Buffer continues to be pumped through chamber 30 until it exits and flows through open valve V4, through tubing 11 and into waste fluid bag 12. All other valves in the system are closed at this time. Buffer continues to be pumped through at Step 1 until a predetermined time and/or volume has been reached and the programmable controller stops the pump 19 and switches the valve sequence to Step 2.

Step 2 delivers the plasma through the affinity media 24, where the lysine ligand selectively binds to the desired blood component, which for illustrative purposes is plasminogen. The plasma is draw out of fluid bag 8 through tubing 7 and through open valve V5. The plasma flows into manifold 21 and through pump chamber 31 driven by pump 19, through open valve V2 and into affinity media chamber 22. The plasma flows out of chamber 22 and through open valve V7. Plasma continues to flow out through tubing 11 and into waste fluid bag 12. All other valves in the system are closed at this time. Plasma continues to be pumped through at Step 2 until a predetermined time, volume, and/or a sensor determined condition has been reached. Then, the programmable controller stops the pump and switches the valve sequence to Step 3.

Step 3 delivers equilibrium buffer to the affinity media chamber 22 to wash the plasma from the chamber 22 along with any unbound proteins, leaving only the bound blood component, namely plasminogen. Buffer is drawn out of fluid bag 9 through tubing 6 and through open valve V1. The buffer flows into manifold 21 and through pump chamber 31 driven by pump 19, through open valve V2 and into affinity media chamber 22. The buffer flows out of chamber 22 and through open valve V7. The buffer continues to flow out through tubing 11 and into waste fluid bag 12. All other valves in the system are closed during Step 3 as detailed in Table 1. Buffer continues to be pumped through at Step 3 until a predetermined time, volume, and/or a sensor determined condition has been reached. Then, the programmable controller stops the pump and switches the valve sequence to Step 4.

Step 4 involves the displacement of the equilibrium buffer from the affinity media chamber 22 and gel chamber 30, and the elution of the plasminogen from the affinity media 24 with a competitive binding solution, such as epsilon aminocaproic acid also occurs in the course of Step 4. Elution solution is withdrawn from fluid bag 10 through tubing 5 and through open valve V6. The elution solution flows into manifold 21 and through pump chamber 31 driven by pump 19, through open valve V2 and into affinity media chamber 22. The elution solution continues through the affinity media chamber 22 flushing the buffer and unbinding the plasminogen, then exiting chamber 22 flowing through open valve V3 and into gel filtration media chamber 30. The solution is molecularly filtered by the gel filtration media 32 by allowing the large molecular weight plasminogen to flow through and the low molecular weight elution molecule to be retarded by entering the pores of the swollen gel beads. Elution solution continues to be pumped through gel media chamber 30 until it exits and flows through open valve V4, through tubing 11 and into waste fluid bag 12. All other valves in the system are closed at this time. Elution solution continues to be pumped through at Step 4 until a predetermined time, volume, and/or a sensor determined condition has been reached and the programmable controller stops the pump 19 and switches the valve sequence to Step 5. At this point in the process the controller preferably allows a dwell time between the elution solution to elute more of the plasminogen from the lysine. Dwell time appears to increase the eluted peak height and therefore the eluted protein. The dwell time is in the range of 5 to 30 minutes.

Step 5 involves the continuation of the plasminogen elution process, with preferably the elution curve staged such that the highest concentration of plasminogen can be collected in a single fraction. It is appreciated that other collection profiles are possible according to the present invention. Elution solution is withdrawn from fluid bag 10 through tubing 5 and through open valve V6. The elution solution flows into manifold 21 and through pump chamber 31 driven by pump 19, through open valve V2 and into affinity media chamber 22. The elution solution will continue through the affinity media chamber unbinding the plasminogen, then exiting chamber 22 flowing through open valve V3 and into gel filtration media chamber 30. Gel filtration media chamber 30 continues to separate the plasminogen from the eluent. The plasminogen solution exits chamber 30 and flows through open valve V12 and into collection chamber 34. The pressure of the incoming fluid displaces plunger 36 of chamber 34 while valves V1, V14, and V15 are open so that the air in the system moved by the displaced collection plunger 36 exits the system through filter 60. Elution solution continues to be pumped through at Step 5 until a predetermined time, volume, and/or a sensor determined condition has been reached and the programmable controller stops the pump and switches the valve sequence to Step 6.

It is appreciated that Steps 4 and/or 5 can be independently controlled by monitoring the component concentration exiting gel filtration media chamber 30. A spectrophotometric light generator and detector at a wavelength overlapping a component absorption, which for plasminogen is illustratively 280 nm, not shown, is adapted to detect the change in absorption in the fluid stream. The absorption signal correlating to the protein concentration. Optionally, the controller is programmed to switch the sequence of the valves when a predetermined protein concentration is reached, in order to insure consistent capture of the protein peak of the elution profile.

Step 6 involves the moving of the collected fraction volume of, for example, approximately 2.6 ml of plasminogen solution from collection chamber 34 to concentration chamber 38. The concentration of the plasminogen solution will be increased by removing a percentage of the aqueous from the solution by concentration media 44. Buffer is drawn from fluid bag 9 through tubing 6 and through open valve V1. The buffer flows into manifold 21 and through pump chamber 31 driven by pump 19, and through open valves V9 and V11. The buffer is used as a hydraulic fluid to displace plunger 36 in collection chamber 34 and move the plasminogen solution out of the chamber 34. When the pressure reaches a preselected level, the plasminogen solution moves out of collection chamber 34 through open valve V13 and into concentration chamber 38, displacing plunger 42. At the same time valve V15 is open so that the air moved by displaced plunger 42 of chamber 38 is vented from the system through filter 60.

Step 7 involves the movement of a concentrated volume of approximately 0.5 ml, based on 2.6 ml plasminogen volume in Step 6 of plasminogen solution from the concentration chamber 38 to final collection vial 62. Collection vial 62 is optionally incorporated into cassette 4 or may be added to the system during setup. Buffer is drawn from fluid bag 9 through tubing 6 and through open valve V1. The buffer flows into manifold 21 and through pump chamber 31 driven by pump 19, and through open valves V9 and V14. The buffer is being used as a hydraulic fluid to displace plunger 42 in chamber 38 and move the concentrated plasminogen solution out of the chamber 38. When the pressure reaches a preselected level, the plasminogen solution moves out of collection chamber 38 through open valve V10, through filter 64, through piercing device 66 and into collection vial 62.

The collected plasminogen is available for a variety of uses and may be converted or activated to plasmin by the addition of an activator such as streptokinase or urokinase. Alternatively the activator is placed in the vial prior to attaching it to cassette 4, so conversion occurs as the final concentrated plasminogen is expressed into the vial 62. The conversion of plasminogen to plasmin occurs in 5–15 minutes at room temperature. The plasmin is now ready for use such as for injection into the eye, or other surgical or research applications.

In an alternate biological component separation, urokinase is isolated from urine as an activator of plasminogen to the enzyme plasmin. A disposable cassette with a single chamber contains affinity media such as an antibody or antibody fraction bound to a rigid support, such as epoxy-activated silica bead. The antibody illustratively including goat anti-human urokinase, Monosan PS075 (Sanbio, The Netherlands). The affinity media is washed with buffer then urine is pumped through the affinity chamber. The urokinase selectively binds to the antibody and then the affinity chamber is flushed of the residual urine and urine constituents. The elution is performed with an acidic citrate buffer that is introduced to the affinity chamber to unbind the urokinase. The peak of the eluted urokinase is collected in a collection vial where neutralization optionally occurs if desired for a particular purpose.

Active plasmin quantification involves conventional techniques such as placing a drop of plasmin solution onto a piece of filter paper treated with a synthetic substrate (D-val-leu-lys-pnitroanilide dihydrochloride, Sigma V-0882). Cleavage of the substrate produces a bright yellow color the intensity of which correlates with the presence of plasmin. Alternatively, a spectrophotometric assay based upon the difference between initial and final optical absorbance multiplied by a constant for the cleavage of the synthetic substrate (D-val-leu-lys-pnitroanilide dihydrochloride) measured at a wavelength of 405 nanometers, is employed. Absorption studies, for example, are performed by adding 950 $\mu$l of lysine buffer and 250 $\mu$l of substrate to a cuvette and zeroing the initial absorbance. 50 $\mu$l of plasmin is then added and the absorbance one minute later is measured as the final absorbance.

The above-described separation of the blood component plasminogen and its subsequent conversion into plasmin is accomplished in the matter of tens of minutes in the operating room or laboratory. The automation allows several plasmin preparations to be performed simultaneously by a single clinical technician. The sterile single use cassette assembly provides a closed system of biologic preparation.

Patents and publications mentioned in the specification are indicative of the levels of those skilled in the art to which the invention pertains. These patents and publications are incorporated herein by reference to the same extent as if each individual patent or publication was specifically and individually incorporated herein by reference.

It will, of course, be understood that different biologic components utilizing different binding agents and different releasing agents may alternatively be used without deviation from the spirit or scope of the present invention. Having described our invention, many modifications thereto will become apparent to those skilled in the art to which it pertains without deviation from the spirit of the invention as defined by the scope of the appended claims.

What is claimed is:

1. A biological fluid processing device comprising:
    a biological fluid container enclosing a biological fluid comprising a biological fluid fraction;
    a rigid cassette comprising at least one biological fluid processing chamber selected from the group consisting of: an affinity media chamber, an ionic exchange chromatography media chamber, a gel media chamber, a concentration chamber, and a collection chamber;
    tubing in fluid communication between said container and said at least one biological fluid processing chamber; and
    a programmable instrument adapted to receive said rigid cassette and selectively allow the biological fluid fraction to move from said container to said at least one biological fluid processing chamber.

2. The device of claim 1 wherein the biological fluid is plasma.

3. The device of claim 1 wherein said biological fluid container is a bag.

4. The device of claim 1 wherein said rigid cassette comprises said affinity media chamber and said collector chamber.

5. The device of claim 1 wherein said rigid cassette comprises said ionic exchange chromatography media chamber and said collector chamber.

6. The device of claim 1 wherein said programmable instrument further comprises a valve actuator having a piston rod, the piston rod in alignment with an aperture in said rigid cassette such that the piston rod compresses said tubing.

7. The device of claim 1 further comprising a buffer container in fluid communication with said at least one biological fluid processing chamber.

8. The device of claim 1 further comprising an elution solution container in fluid communication with said at least one biological fluid processing chamber.

9. The device of claim 7 further comprising a manifold receiving fluid inlet from said biological fluid container and said buffer container, said manifold transmitting fluid communication to said at least one biological fluid processing chamber.

10. The device of claim 1 further comprising a waste container downstream from and in fluid communication with said at least one biological fluid processing chamber.

11. The device of claim 1 wherein said programmable instrument comprises a pump for urging the biological fluid fraction into said rigid cassette.

12. The device of claim 11 wherein said pump is a rotary pump.

13. The device of claim 1 wherein said programmable instrument further comprises a sensor for detecting a purified biological component derived from the liquid biological fraction.

* * * * *